United States Patent [19]

Hefner, Jr. et al.

[11] Patent Number: 4,636,542
[45] Date of Patent: Jan. 13, 1987

[54] IMIDE FUNCTIONAL POLYPHENOLS; THERMOSETTABLE COMPOSITIONS CONTAINING SAME AND CURED PRODUCTS THEREFROM

[75] Inventors: Robert E. Hefner, Jr.; Mary N. White, both of Lake Jackson, Tex.

[73] Assignee: The Dow Chemical Company, Midland, Mich.

[21] Appl. No.: 773,895

[22] Filed: Sep. 9, 1985

Related U.S. Application Data

[62] Division of Ser. No. 679,529, Dec. 7, 1984, Pat. No. 4,555,563.

[51] Int. Cl.$^4$ ............................................. C08G 59/26
[52] U.S. Cl. ................................... 523/466; 523/468; 525/422; 525/423; 528/96; 528/97; 528/104

[58] Field of Search ................. 525/422, 423; 528/96, 528/97, 104; 523/468, 466

[56] References Cited

U.S. PATENT DOCUMENTS

| 4,038,251 | 7/1977 | Forgo et al. | 528/170 |
| 4,401,777 | 8/1983 | Tsuboi et al. | 528/322 X |
| 4,510,272 | 4/1985 | Loszewski | 528/322 X |
| 4,558,115 | 12/1985 | Hefner | 528/322 X |

Primary Examiner—Earl Nielsen
Attorney, Agent, or Firm—James G. Carter

[57] ABSTRACT

Imide functional polyphenols are prepared by reacting an excess of a phenol with an unsaturated diimide which is prepared by reacting an unsaturated polycycloaliphatic dicarboxylic acid anhydride with a diamine.

These materials are useful in the preparation of castings, coatings, laminates and the like.

13 Claims, No Drawings

IMIDE FUNCTIONAL POLYPHENOLS; THERMOSETTABLE COMPOSITIONS CONTAINING SAME AND CURED PRODUCTS THEREFROM

This is a divisional of application Ser. No. 679,529, filed Dec. 7, 1984, now U.S. Pat. No. 4,555,563.

BACKGROUND OF THE INVENTION

The present invention pertains to new compositions of matter, to novel thermosettable compositions containing them and to cured products therefrom.

Thermosettable compositions such as polycyanates and polyepoxides are well known. Typical of these compositions are bisphenol A dicyanate and the diglycidyl ether of bisphenol A. Such compositions are useful in the preparation of castings, laminates, coatings and the like, with many desirable properties. However, there is room for improvement in the mechanical properties and physical properties, such as moisture resistance, of said castings, laminates, coatings, and the like.

The present invention provides a class of novel imide functional polyphenols as well as thermosettable polycyanates and polyepoxides thereof. The thermoset (cured) resins have an improvement in one or more properties such as hardness, flexural strength, flexural modulus, resistance to moisture, and the like.

SUMMARY OF THE INVENTION

The present invention is directed to new compositions of matter represented by the formulas:

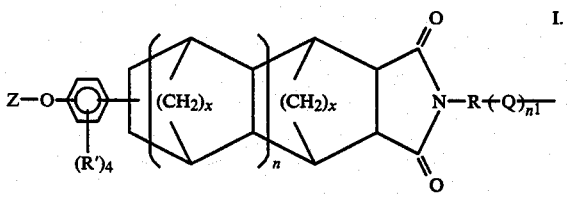

I.

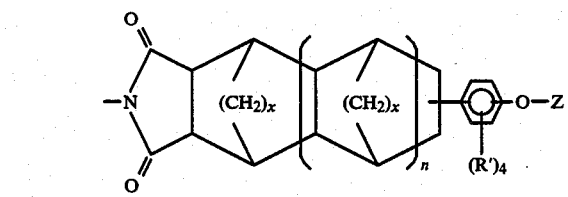

II.

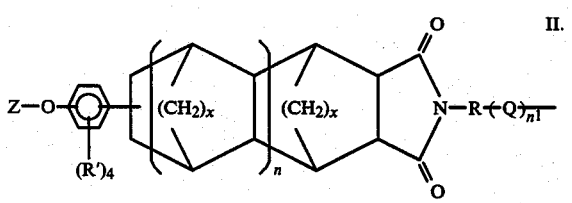

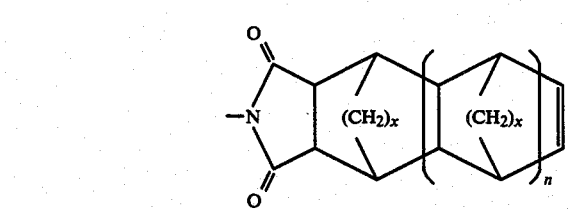

wherein each Q is independently

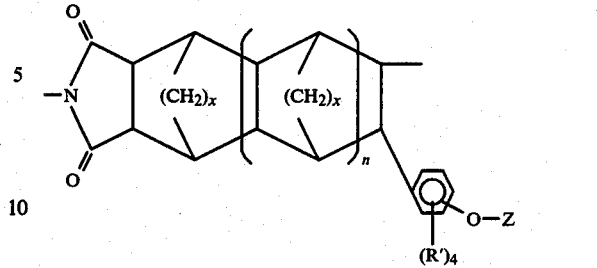

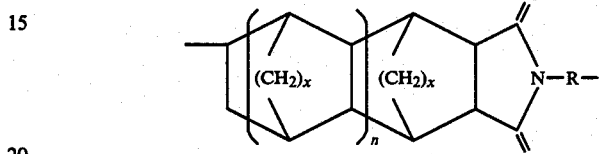

or

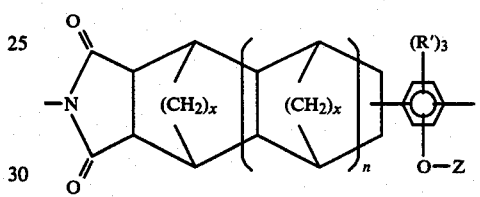

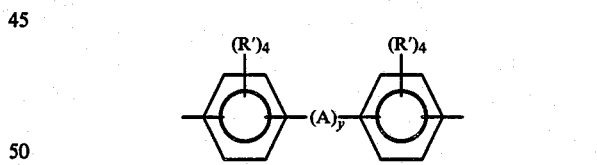

each R is independently a hydrocarbyl group having from 1 to about 10, preferably from 2 to about 5 carbon atoms or a

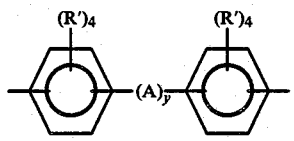

group; each A is independently a divalent hydrocarbyl group having from 1 to about 10, preferably from about 1 to about 4 carbon atoms, $-S-$, $-S-S-$, $-O-$,

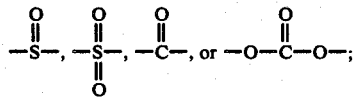

each R' is independently hydrogen, chlorine, bromine, a hydrocarbyl or hydrocarbyloxy group having from 1 to about 3 carbon atoms; each R'' is hydrogen or a hydrocarbyl group having from 1 to about 3 carbon atoms; Z is independently hydrogen or a group represented by the formulas

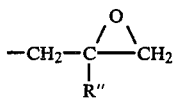

or —C≡N, each x has a value of zero or 1; each y has a value of zero or 1; each n independently has an average value from zero to about 20, preferably from zero to or —C≡N group.

The present invention also concerns polyepoxide compositions which are thermosettable upon curing with a curing quantity of a suitable curing agent. Said polyepoxide compositions are prepared by advancement reaction (copolymerization) of the compositions represented by Formulas I or II wherein each Z is hydrogen, with a polyepoxide of Formulas III, IV, V, VI or a mixture thereof

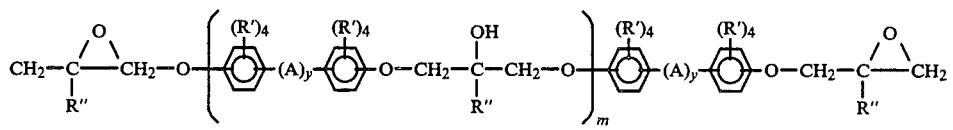

III.

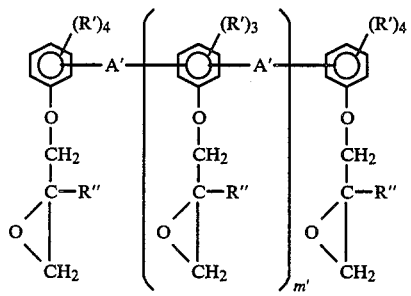

IV.

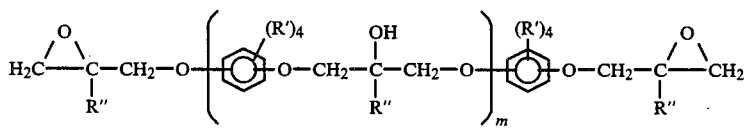

V.

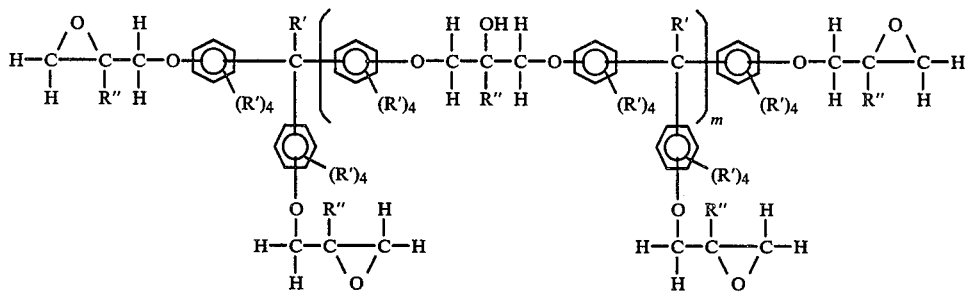

VI.

about 8, and $n^1$ has a value from zero to about 10, preferably from zero to about 2.

The major component (about 75 to 100 percent) of these compositions is represented by Formula I where $n^1$ has a value of zero, while minor components (0 to about 25 percent) are represented by Formulas I and II where $n^1$ has a value from 1 to about 10. All of the compositions represented by Formulas I and II are isomeric mixtures wherein the substitution of the phenolic (or substituted phenoxy) groups by the norbornyl group is in the ortho and para positions.

The present invention also concerns thermosettable (curable) compositions of the compositions represented by Formulas I or II wherein each Z is a

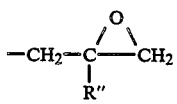

wherein each R', R", y and are as hereinbefore defined; each A' is independently a divalent hydrocarbyl group having from 1 to about 10, preferably from 1 to about 4 carbon atoms; m has a value of from zero to about 40, preferably from zero to about 10; and m' has a value of from about 0.001 to about 10, preferably from about 0.01 to about 3.

The present invention also concerns polyepoxide compositions prepared by reacting a composition represented by Formulas I or II wherein each Z is

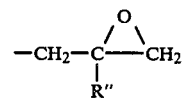

with a phenolic material represented by Formulas VII, VIII, IX, X or a mixture thereof.

VII.

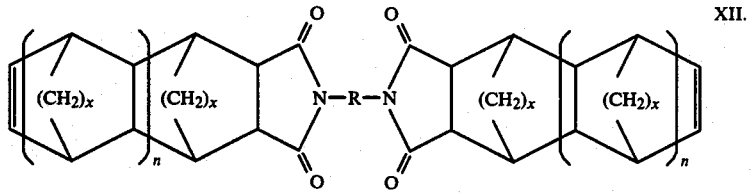

XI.

XII.

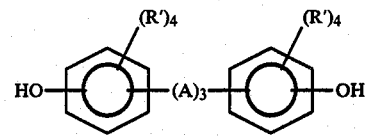

VIII.

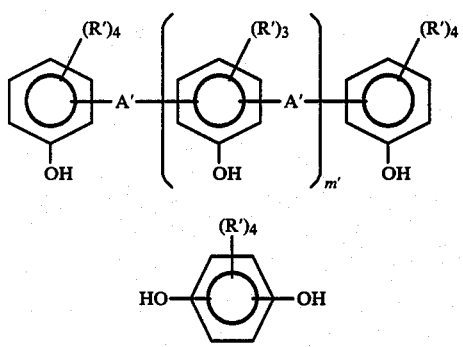

IX.

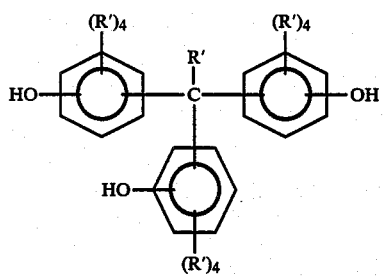

X.

rated diimide of the structure represented by Formula XII in the presence of an acidic catalyst.

wherein each R, R', x and n are as hereinbefore defined, and with the proviso that at least one ortho or para R' in formula XI is a hydrogen.

The unsaturated diimide represented by Formula XII is obtained by condensation reaction of an unsaturated polycycloaliphatic dicarboxylic acid anhydride of the structure represented by Formula XIII with a diamine of the structure represented by Formula XIV, XV or a mixture thereof.

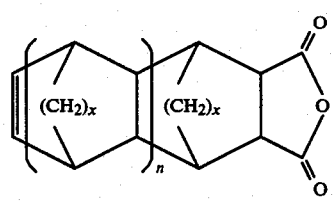

XIII.

XIV.

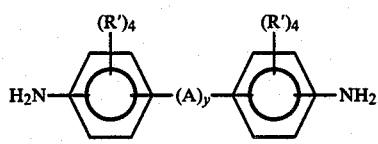

XV.

wherein each A, R, R', y, x and n are as hereinbefore defined.

In the compositions represented by Formulas I and II when n is zero and x is 1, the unsaturated polycycloaliphatic dicarboxylic acid anhydride represented by Formula XIII is endomethylenetetrahydrophthalic anhydride (carbic anhydride). In the compositions represented by Formulas I and II when n is zero and x is zero, the unsaturated polycycloaliphatic dicarboxylic acid anhydride represented by Formula XIII is tetrahydrophthalic anhydride. In the compositions represented by Formulas I and II when n has a value of 1 to about 20, the unsaturated polycycloaliphatic dicarboxylic acid anhydride represented by Formula XIII is a Diels-Alder adduct of an unsaturated dicarboxylic acid anhydride and a diolefin. As a specific example, reaction of a 10 to 1 mole ratio of cyclopentadiene with maleic anhydride provides an unsaturated polycycloaliphatic dicarboxylic acid anhydride represented by Formula XIII wherein n has a value of 1 to about 10 and x is 1.

The imide functional polyphenols are prepared by reacting a phenol represented by Formula XI and an unsaturated diimide represented by Formula XII at a reaction temperature of from about 75° C. to about 175° C. with reaction temperatures of 100° C. to 155° C.

wherein each A, A', R', m' and y are as hereinbefore defined.

The present invention also concerns polyepoxide compositions prepared by reacting a composition represented by Formulas I or II wherein each Z is a

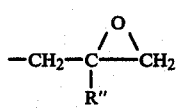

group with a material represented by Formulas I or II or a mixture thereof wherein each Z is a hydrogen.

The present invention also concerns cured and curable compositions thereof.

DETAILED DESCRIPTION OF THE INVENTION

The imide functional polyphenols can be prepared by the reaction of a stoichiometric excess of a phenol of the structure represented by Formula XI with an unsatubeing preferred. If desired, inert solvents such as xylene can be employed. Typical acidic catalysts include boron trifluoride etherate, acid ion exchange resins, and Filtrol 1 (an acidified clay manufactured by Filtrol Corporation).

The imide functional polyphenols wherein the compositions represented by Formula I (Z is hydrogen) are present at 95 percent or more require the use of a mole ratio of phenol (Formula XI) to unsaturated diimide (Formula XII) of about 10 to 1, preferably about 15 to 1. The imide functional polyphenols wherein the compositions represented by Formula II are present at 5 to about 20 percent or more require the use of a mole ratio of phenol (Formula XI) to unsaturated diimide (Formula XI) of less than 10 to 1, preferably about 8 to about 4 to 1. At mole ratios below 8 to 1, unreacted unsaturated diimide (Formula XII) also remains in the product.

Excess (unreacted) phenol may be removed from the imide functional polyphenols by vacuum distillation, azeotropic distillation, extraction or a combination of these methods. Because of its ease of removal, phenol, per se, is a most preferred reactant as represented by Formula XI.

The polyepoxide compositions of the imide functional polyphenols are represented by Formulas I and II wherein Z is

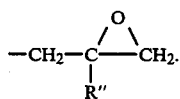

Said compositions are prepared using epoxidation methods described in *Handbook of Epoxy Resins* by Lee and Neville, McGraw-Hill, 1967 which is incorporated herein by reference. This usually includes reacting the imide functional polyphenol (Formulas I or II where Z is hydrogen) with an epihalohydrin followed by dehydrohalogenation with a basic-acting material such as an alkali metal hydroxide and finally recovering the resultant glycidyl ether product.

Suitable curing agents and/or catalysts for the polyepoxide compositions are described in the aforementioned *Handbook of Epoxy Resins*.

The polyepoxide compositions of the imide functional polyphenols (Formulas I or II where Z is a

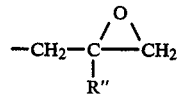

group) can be mixed with 1 to 99 percent by weight (pbw), preferably 40 to 80 pbw of a polyepoxide composition (Formulas III, IV, V, VI or a mixture thereof) and then cured as previously described.

The polycyanate compositions of the imide functional polyphenols are represented by Formulas I and II where Z is a —C≡N group. Said compositions are prepared by reaction of an imide functional polyphenol (Formulas I or II where Z is hydrogen) with a cyanogen halide in the presence of a suitable base.

Suitable cyanogen halides which can be employed herein include, for example, cyanogen chloride, cyanogen bromide, mixtures thereof and the like.

If desired, the method reported in *Organic Syntheses*, Vol. 61, pages 35-37 (1983), published by John Wiley and Sons, may be used to generate the required amount of cyanogen halide in situ, although this is less preferred than using neat cyanogen halide.

Suitable base materials which can be employed herein include both inorganic bases and tertiary amines, such as, for example, sodium hydroxide, potassium hydroxide, triethylamine, mixtures thereof and the like. The tertiary amines are most preferred as the base material.

The reaction is usually conducted at a temperature of from about −40° C. to about 60° C., preferably from −20° C. to about 25° C. for from about 10 minutes (600 s) to about 120 minutes (7200 s), preferably from about 10 minutes (600 s) to about 60 minutes (3600 s).

The reaction is preferably conducted in the presence of an inert solvent reaction medium. Suitable such solvents include, for example, water, chlorinated hydrocarbons, ketones, mixtures thereof and the like. Acetone or methylene chloride are most preferred as the inert solvent reaction medium.

A mole ratio of from about 1.2 to 1.0, preferably 1.1 to 1.0 cyanogen halide per phenolic hydroxyl group is employed. A mole ratio of from about 1.2 to 1.0, preferably 1.05 to 1.0 of the base material per phenolic hydroxyl group is employed.

The polycyanate compositions of the imide functional polyphenols represented by Formulas I and II where Z is a —C≡N group are thermoset (cured) using a curing quantity of a suitable curing agent to provide polymers containing the triazine group. Suitable curing agents which can be employed herein include, for example, metal salts of carboxylic acids, such as, lead octoate, zinc stearate, zinc acetylacetonate, at concentrations of about 0.001 to 5 percent by weight. Most preferred catalysts are cobalt naphthenate and cobalt octoate, mixtures thereof and the like. Curing is usually conducted at a temperature of from about 70° C. to about 350° C., preferably from about 70° C. to about 200° C. for a period of from about 15 minutes (900 s) to about 120 minutes (7200 s), preferably from about 30 minutes (1800 s) to about 75 minutes (4500 s). The polycyanate compositions of the imide functional polyphenols also may be cured without the use of a curing agent, however, longer times and higher temperatures are typically required.

The polycyanate compositions of the imide functional polyphenols (Formulas I and II wherein Z is a —C≡N group) can be mixed with 1 to 99 pbw, preferably 50 to 90 pbw of a polycyanate composition represented by Formulas XVI, XVII, XVIII, XIX or a mixture thereof

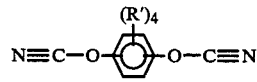

XVI.

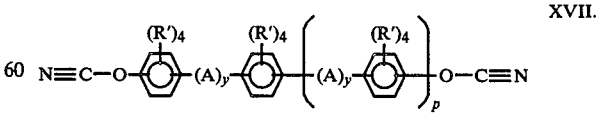

XVII.

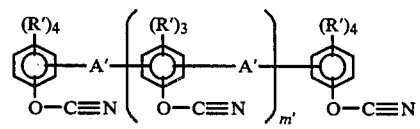

XVIII.

-continued

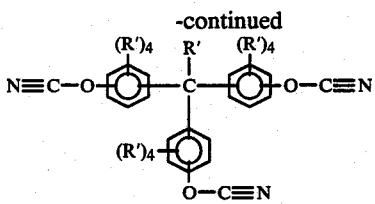

XIX.

wherein R', A, A', y and m' are as hereinbefore defined and p has a value of zero to about 100, preferably from zero to about 10. Curing of the polycyanate mixture is accomplished as previously described.

The polycyanate compositions of the imide functional polyphenols (Formulas I and II wherein Z is a —C≡N group) can be mixed with a polyepoxide composition (Formulas III, IV, V, VI or a mixture thereof) and the mixture then cured using the methods previously described for the polycyanate compositions, per se. One or more of the polycyanate compositions represented by Formulas XVI, XVII, XVIII or XIX may also be added to the aforesaid polycyanate and polyepoxide mixture(s). If the polycyanate and polyepoxide are combined stoichiometrically (a one to one mole ratio of —C≡N to

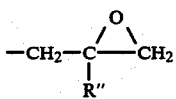

groups is provided) then cured polymers containing the oxazoline group are provided. If the polycyanate and less than stoichiometric polyepoxide are combined then cured polymers containing both oxazoline and triazine groups are provided.

Polyepoxide compositions are prepared, for example, by advancement reaction (copolymerization) of the imide functional polyphenols (Formulas I or II wherein each Z is hydrogen) and a polyepoxide composition (Formulas III, IV, V, VI or a mixture thereof) in the presence of a suitable catalyst. Suitable catalysts which can be employed herein include, for example, the quaternary ammonium salts, phosphonium salts, mixtures thereof and the like. A most preferred catalyst is benzyltrimethylammonium chloride.

The advancement reaction is usually conducted at a temperature of from about 80° C. to about 200° C., preferably about 100° C. to about 150° C. for from about 10 minutes (600 s) to about 120 minutes (7200 s), preferably from about 30 minutes (1800 s) to about 60 minutes (3600 s).

A mole ratio of from about 0.01 to 0.99, preferably 0.05 to 0.30 of phenolic hydroxyl group per epoxide group is used in the advancement reaction.

Curing of the polyepoxide compositions from the advancement reactions is accomplished as previously described for the polyepoxide compositions, per se.

The cured compositions of the present invention can be used to prepare castings, laminates or composites, coatings, preimpregnated fabrics or cloths, encapsulations and the like, and are especially suited for use in environments demanding high mechanical strength and moisture resistance.

The following examples are illustrative of the invention, but are not to be construed as to limiting the scope thereof in any manner.

EXAMPLE 1

A. Preparation of Unsaturated Diimide

A solution of 1,2-diaminoethane (49.5 grams, 0.825 mole) and dimethylformamide (300 milliliters) was heated to 60° C. with stirring and maintained under a nitrogen atmosphere. Endomethylenetetrahdyrophthalic anhydride (270.0 grams, 1.65 moles) was added to the reactor over a 45-minute (2700 s) period after which time the reactor was heated to 100° C. and held for 60 minutes (3600 s). The reaction temperature was then increased to 120° C. and held for 240 minutes (14,400 s). After this time, no further water was being recovered into the Dean Stark trap-cold water condenser assembly, hence the reactor was cooled to room temperature (26° C.). The reaction product was dissolved in hot tetrahydrofuran solvent and then allowed to stand overnight. The crystalline product was removed by filtration and twice-washed with a 50-50 percent by volume mixture of methylene chloride and methanol. The white crystals were dried under vacuum for 12 hours (42,300 s) at 86° C. until a constant product weight of 212.5 grams (73 percent yield) was recovered. Infra-red spectrophotometric analysis and nuclear magnetic resonance spectroscopy confirmed the product structure for the diimide of endomethylenetetrahydrophthalic anhydride.

B. Preparation of Imide Functional Polyphenol

Phenol (285.0 grams, 3.0 moles) and boron trifluoride etherate (4.0 grams) were heated to 110° C. with stirring and maintained under a nitrogen atmosphere. A portion of the diimide of endomethylenetetrahydrophthalic anhydride (70.4 grams, 0.20 mole) was added to the reactor and the reaction temperature was increased to 150° C. and held for 180 minutes (10,800 s). After this time, the excess phenol was vacuum distilled from the reactor. The reactor was then cooled to room temperature (26° C.) then water (90 milliliters) was added and then removed by rotary evaporation. t-Butanol (100 milliliters) was then added and phenol plus t-butanol azeotrope removed by rotary evaporation. The product was placed in a 9-inch by 6-inch flat glass tray and dried under vacuum (50 millimeters Hg) for 24 hours (86,400 s) at 120° C. The polyphenol of the diimide of endomethylenetetrahydrophthalic anhydride (109 grams, 99 percent yield) was recovered as a light yellow colored, brittle, transparent solid. Infra-red spectrophotometric analysis, nuclear magnetic resonance spectroscopy and liquid chromatographic analysis confirmed the product structure.

C. Preparation of Polycyanate of the Imide Functional Polyphenol

Cyanogen bromide (38.14 grams, 0.3601 mole) was added to a reactor containing stirred chloroform (60 milliliters) under a nitrogen atmosphere. The cyanogen bromide-chloroform solution was cooled to −5° C. then a portion of the diimide polyphenol (92.0 grams, 0.1715 mole) dissolved in chloroform (282 milliliters) was added to the reactor. The stirred solution was allowed to equilibrate at −5° C. then triethylamine (34.88 grams, 0.3447 mole) was added to the reactor over a 20-minute (1200 s) period and so as to maintain the reaction temperature at −5° to 0° C. After completion of the triethylamine addition, the reaction temperature was maintained at −1° to 6° C. for an additional 30 minutes (1800 s) followed by addition of the reaction product to chilled water (1200 milliliters) with agitation. After 5 minutes (300 s), the water and product mixture was added to a separatory funnel and the organic layer recovered. The organic layer was washed with 5 percent hydrochloric acid (400 milliliters), water (800 milliliters) and then dried over anhydrous sodium sulfate. The dry chloroform extract was filtered and solvent removed by rotary evaporation under vacuum. The polycyanate of the polyphenol of the diimide of endomethylenetetrahydrophthalic anhydride was recovered as a light yellow colored, brittle, transparent solid. Infra-red spectrophotometric analysis and nuclear magnetic resonance spectroscopy confirmed the product structure.

COMPARATIVE EXPERIMENT A

Preparation of Bisphenol A Dicyanate

A quantity of 222.45 grams (2.10 moles) of cyanogen bromide was added to a reactor containing 350 milliliters of stirred acetone under a nitrogen atmosphere. The cyanogen bromide-acetone solution was cooled to −5° C., then 228.30 grams (1.0 mole) of Bisphenol A dissolved in 700 milliliters of chilled acetone was added to the reactor. The stirred solution was allowed to equilibrate at −5° C., then 203.39 grams of triethylamine (2.01 moles) was added to the reactor over a 24-minute (1440 s) period and so as to maintain the reaction temperature at −5° C. to 0° C. After completion of the triethylamine addition, the reactor was maintained at −11° to 1° C. for 40 minutes (2400 s), followed by addition of the reaction product to 3600 milliliters of chilled water with agitation. After 5 minutes (300 s), the water and product mixture was multiply extracted with methylene chloride. The combined methylene chloride extracts were sequentially washed with dilute 5 percent hydrochloric acid, water, dilute hydrochloric acid, water and then dried over anhydrous magnesium sulfate. The dry methylene chloride extract was filtered and solvent removed by rotary evaporation under vacuum. Bisphenol A dicyanate, 265.5 grams, was recovered in 95.4 percent yield as a light tan colored crystalline solid. Infra-red spectrophotometric analysis confirmed the product structure.

Prior to use, the Bisphenol A dicyanate was recrystallized from acetone then dried in a vacuum oven to provide a white crystalline solid.

EXAMPLE 2

A pair of 12 in. × 12 in. (304.8 mm × 304.8 mm) woven fiberglass cloth pieces were equally impregnated with a solution prepared from 10.0 grams of the polycyanate diimide of Example 1-C, 40.0 grams of Bisphenol A dicyanate of Comparative Experiment A, 100 grams of chloroform, and 0.166 gram of cobalt naphthenate (6.0 percent active). The fiberglass cloth used was a commercial-grade product treated with a proprietary coupling agent (Burlington 76-28 electrical laminating cloth) and had an average weight of 0.14 gram per square inch (0.0217 g/cm$^2$). The pair of impregnated fiberglass cloths were allowed to dry for 24 hours (86,400 s) at room temperature (25° C.) followed by prepolymerization (B-staging) in a vented, forced-air, convection-type oven for 10 minutes (600 s) at 70° C., 10 minutes (600 s) at 100° C., then 20 minutes (1200 s) at 150° C. Each cloth was cooled, found to be tack-free at room temperature and then cut to provide eight 6 in.×6 in. (152.4 mm×152.4 mm) pieces. The pieces were stacked into a 6 in.×6 in.×1/16 in. (152.4 mm×152.4 mm×1.5875 mm) stainless steel frame and placed between stainless steel plates which had been coated with a silicone mold release. The plates were loaded into a 177° C. hot press (Pasadena Hydraulics, Inc., Model P-215) and maintained for two hours (7200 s) at 5000 psi (34.5 MPa). After this time a 6 in.×6 in.×1/16 in. (152.4 mm×152.4 mm×1.5875 mm) light amber-colored, semi-transparent, rigid laminate was recovered and cut to provide a set of four 1 in.×2 in.×1/16 in. (25.4 mm×50.8 mm×1.5875 mm) flexural strength test pieces. The flexural strength test pieces were post-cured at 200° C. for two hours (7200 s) and then tested on an Instron machine with standard methods (ASTM D-790). The Instron machine was set at a 1 in. (25.4 mm) span, 0.02 in. per minute (0.00085 cm/s) crosshead speed and a 0.5 in. per minute (0.021166 cm/s) chart speed. The Barcol hardness value is on the 934-1 scale. The results are reported in Table I.

COMPARATIVE EXPERIMENT B

A pair of 12 in. × 12 in. (304.8 mm × 304.8 mm) woven fiberglass cloth pieces were equally impregnated with a solution prepared from 50.0 grams of Bisphenol A dicyanate of Comparative Experiment A, 100 grams of chloroform and 0.166 grams of cobalt naphthenate (6.0 percent active). Prepolymerization (B-staging), post-curing, laminate fabrication and mechanical property testing were completed using the method of Example 2 to provide a tack-free cloth at room temperature. The laminate thus obtained was rigid, white-colored and semi-transparent. The results are reported in Table I.

TABLE I

|  | Example 2 | Comparative Experiment B |
| --- | --- | --- |
| Barcol Hardness | 46 | 42 |
| Flexural Strength, |  |  |
| psi | 55.4 × 10$^3$ | 48.5 × 10$^3$ |
| kPa | 382 × 10$^3$ | 334 × 10$^3$ |
| Flexural Modulus, |  |  |
| psi | 3.05 × 10$^6$ | 2.93 × 10$^6$ |
| kPa | 21.0 × 10$^6$ | 20.2 × 10$^6$ |

EXAMPLE 3

A. Preparation of Unsaturated Diimide

A solution of 1,2-diaminoethane (80.8 grams, 1.34 moles) and dimethylformamide (450 milliliters) was heated to 60° C. with stirring and maintained under a nitrogen atmosphere. Endomethylenetetrahydrophthalic anhydride (441.0 grams, 2.68 moles) was added to the reactor over a 90 minute (5400 s) period in 30 to 40 gram aliquots so as to maintain the reaction temperature between 90° and 100° C. After the 90 minute (5400 s) addition time was complete, the reactor was heated to 110° C. and held for 30 minutes (1800 s). The reaction temperature was then increased to 155° C. and held for 120 minutes (7200 s). After this time no further water was being recovered into the Dean Stark trap-cold water condenser assembly, hence the reactor was cooled to room temperature (26° C.). The reaction product was mixed with methanol and the resulting crystalline product was removed by filtration and triple-washed with methanol. The white crystals were dried for 12 hours (43,200 s) at 120° C. under vacuum (50 millimeters Hg) until a constant product weight of 226 grams (70.4 percent yield) was recovered. Infra-red spectrophotometric analysis and nuclear magnetic resonance spectroscopy confirmed the product structure for the diimide of endomethylenetetrahydrophthalic anhydride.

B. Preparation of Imide Functional Polyphenol

Phenol (520.0 grams, 5.53 moles) and boron trifluoride etherate (6.0 grams) were heated to 110° C. with stirring and maintained under a nitrogen atmosphere. A portion of the diimide of endomethylenetetrahydro phthalic anhydride (127.0 grams, 0.361 mole) was added to the reactor and the reaction temperature was increased to 145° C. and held for 180 minutes (10,800 s), then to 155° C. for 60 minutes (3600 s). After this time, the excess phenol was vacuum distilled from the reactor (100° C. and 5 millimeter Hg). The product was then powdered and extracted with 90° C. water (2 liters). The product was then placed in a 9 inch by 6 inch (228.6 mm×152.4 mm) flat glass tray and dried under vacuum (50 millimeters Hg) for 16 hours (57,600 s) at 120° C. The polyphenol of the diimide of endomethylenetetrahydrophthalic anhydride (209 grams, 99 percent yield) was recovered as a light yellow colored, brittle, transparent solid. Infra-red spectrophotometric analysis, nuclear magnetic resonance spectroscopy and liquid chromatographic analysis confirmed the product structure.

C. Preparation of Polycyanate of the Imide Functional Polyphenol

A portion of the diimide polyphenol (72.97 grams, 0.1360 mole) dissolved in chloroform (271.3 milliliters) was added to a reactor and stirred under a nitrogen atmosphere. The diimide polyphenol-chloroform solution was cooled to −5° C. then cyanogen bromide (30.25 grams, 0.2856 mole) was added to the reactor. The stirred solution was allowed to equilibrate at −5° C. then triethylamine (27.66 grams, 0.2734 mole) was added to the reactor over a 15-minute (900 s) period and so as to maintain the reaction temperature at −6° to −2° C. After completion of the triethylamine addition, the reaction temperature was maintained at −2° to 5° C. for an additional 30 minutes (1800 s), followed by addition of the reaction product to chilled water (1000 milliliters) with agitation. After 5 minutes (300 s) the water and product mixture was added to a separatory funnel and the organic layer recovered. The organic layer was washed with 5 percent hydrochloric acid (300 milliliters), water (500 milliliters), and then dried over anhydrous sodium sulfate. The dry chloroform extract was filtered and solvent removed by rotary evaporation under vacuum. The polycyanate of the polyphenol of the diimide of endomethylenetetrahydrophthalic anhydride was recovered (79.8 grams) in 100 percent yield as a light yellow colored, brittle, transparent solid. Infrared spectrophotometric analysis and nuclear magnetic resonance spectroscopy confirmed the product structure.

COMPARATIVE EXPERIMENT C

Preparation of Bisphenol A Dicyanate

A quantity of 222.45 grams (2.10 moles) of cyanogen bromide was added to a reactor containing 350 milliliters of stirred acetone under a nitrogen atmosphere. The cyanogen bromide-acetone solution was cooled to −5° C., then 228.30 grams (1.00 mole) of Bisphenol A dissolved in 700 milliliters of chilled acetone was added to the reactor. The stirred solution was allowed to equilibrate at −5° C., then 203.39 grams (2.01 moles) of triethylamine was added to the reactor over a 25-minute (1500 s) period and so as to maintain the reaction temperature at −5° to 0° C. After completion of the triethylamine addition, the reaction temperature was maintained at −6° to 7° C. for an additional 45 minutes (2700 s), followed by addition of the reaction product to chilled water (1 gallon, 3.78 liters) with agitation. After 20 minutes (1200 s), the water and product mixture was added to a separatory funnel and the resulting slurry of crystals was filtered. The recovered crystalline product was dissolved in methylene chloride (400 milliliters), washed with 5 percent hydrochloric acid (500 milliliters), washed with water (1000 milliliters) and then dried over anhydrous sodium sulfate. The dry methylene chloride solution was filtered and solvent removed by rotary evaporation under vacuum. Bisphenol A dicyanate (245.3 grams) was recovered in 88.1 percent yield as a light tan colored crystalline solid. Infra-red spectrophotometric analysis confirmed the product structure.

EXAMPLE 4

A pair of 12 in.×12 in. (304.8 mm×304.8 mm) woven fiberglass cloth pieces were equally impregnated with a solution prepared from 12.5 grams of the polycyanate diimide of Example 3-C, 37.5 grams Bisphenol A dicyanate of Comparative Experiment C, chloroform (100 grams) and cobalt naphthenate (0.166 grams, 6.0 percent active).

The fiberglass cloth used was a commercial-grade product treated with a proprietary coupling agent (Burlington 76-28 electrical laminating cloth) and had an average weight of 0.14 gram per square inch (0.0217 g/cm$^2$). The pair of impregnated fiberglass cloths was allowed to dry for 24 hours (86,400 s) at room temperature (25° C.) followed by prepolymerization (B-staging) in a vented, forced air, convection-type oven for thirty minutes (1800 s) at 70° C., twenty-three minutes (1380 s) at 90° C., 10 minutes (600 s) at 110° C., then fourteen minutes (840 s) at 150° C. Each cloth was cooled, found to be tack-free at room temperature and then cut to provide eight 6 in.×6 in. (152.4 mm×154.4 mm) pieces. The pieces were stacked into a 6 in.×6 in.×1/16 in. (154.4 mm×152.4 mm×1.5874 mm) stainless steel frame and placed between stainless steel plates which had been coated with a silicone mold release. The plates were loaded into a 200° C. hot press (Pasadena Hydraulics Inc., Model P-215) and maintained for 2 hours (7200 s) at 5000 psi (34.5 MPa). After this time, a 6 in.×6 in.×1/16 in. (152.4 mm×152.4 mm×1.5875 mm) light yellow-colored, transparent, rigid laminate was recovered and cut to provide a set of four 1 in.×2 in.×1/16 in. (25.4 mm×50.8 mm×1.5875 mm) flexural strength test pieces. Post-curing and mechanical property testing was completed using the method of Example 2. The results are reported in Table II.

TABLE II

|  | Example 4 |
| --- | --- |
| Barcol Hardness | 64 |
| Flexural Strength, | |
| psi | 72.9 × 10$^3$ |
| kPa | 503 × 10$^3$ |
| Flexural Modulus, | |
| psi | 2.65 × 10$^6$ |
| kPa | 18.3 × 10$^6$ |

EXAMPLE 5

A commercial grade of bisphenol A diglycidyl ether (219.60 grams, 0.60 mole) having an epoxide equivalent weight (EEW) of 183 was reacted with the diimide polyphenol (53.65 grams, 0.10 mole) of endomethylenetetrahydrophthalic anhydride and 1,2-diaminoethane to provide an advanced epoxy resin with imide functionality. The diimide polyphenol was prepared using the method of Example 1-A and B scaled up 2.1 fold and with the single exception that the t-butanol azeotropic distillation step was omitted from the workup. The diimide polyphenol, bisphenol A diglycidyl ether and 60 percent aqueous benzyltrimethylammonium chloride catalyst (0.27 gram) were added to a reactor and heated to 120° C. with stirring under a nitrogen atmosphere. After 60 minutes (3600 s) at the 120° C. reaction temperature, the reactor was cooled and the imide functional advanced epoxy resin was recovered as a transparent, light amber colored liquid. Epoxide titration revealed 17.54 percent epoxide in the resin. A portion of the epoxy resin (269.23 grams) was heated to 75° C. then methylene dianiline (54.36 grams) was added and thoroughly mixed in. This solution was used to prepared a clear, unfilled ⅛ inch (3.175 mm) casting for heat distortion temperature (264 psi, 1820 MPa), tensile and flexural strength, flexural modulus, percent elongation, and Barcol hardness (934-1 scale) determinations. The casting was cured for 2 hours (7200 s) at 75° C. followed by post curing for 2 hours (7200 s) at 125° C., 2 hours (7200 s) at 175° C., then 2 hours (7200 s) at 200° C. Mechanical properties of tensile (8) and flexural (6) test pieces were determined using an Instron machine with standard test methods (ASTM D-638 and D-790). Heat distortion temperature of clear casting test pieces (2) was determined using an Aminco Plastic Deflection Tester (American Instrument Co.) with standard test methods (ASTM D-648 modified). The results are reported in Table III.

COMPARATIVE EXPERIMENT D

A commercial grade of bisphenol A diglycidyl ether (292.80 grams, 0.80 mole) having an EEW of 183 was reacted with bisphenol A (30.44 grams, 0.1333 mole) to provide an advanced epoxy resin. The bisphenol A, bisphenol diglycidyl ether and 60 percent aqueous benzyltrimethylammonium chloride catalyst (0.32 gram) were added to a reactor and heated to 120° C. with stirring under a nitrogen atmosphere. After 60 minutes (3600 s) at the 120° C. reaction temperature, the reactor was cooled and the bisphenol A advanced epoxy resin was recovered as a transparent, light yellow colored liquid. Epoxide titration revealed 17.54 percent epoxide (EEW=245) in the resin.

A portion of the epoxy resin (316.37 grams) was heated to 75° C. then methylenedianiline (62.08 grams) was added and thoroughly mixed in. This solution was used to prepare a clear, unfilled ⅛ inch (3.175 mm) casting using the method of Example 5. Physical and mechanical properties were evaluated using the method of Example 5. The results are reported in Table III.

TABLE III

|  | Example 5 | Comparative Experiment D |
|---|---|---|
| Barcol Hardness | 46 | 38 |
| Heat Distortion Temperature, °C./°F. | 140.5/284.9 | 139.5/283.1 |
| Tensile Strength, | | |
| psi | 10,401 | 11,269 |
| kPa | 71,700 | 77,700 |
| Elongation % | 2.70 | 3.51 |
| Flexural Strength, | | |
| psi | 17,353 | 19,734 |
| kPa | 120,000 | 136,000 |
| Flexural Modulus, | | |
| psi | 573,000 | 420,000 |
| kPa | $3.95 \times 10^6$ | $2.90 \times 10^6$ |

EXAMPLE 6

A set of flexural test pieces (3) were prepared from a portion of the clear, unfilled casting of Example 5. Each test piece was numbered and weighed and then placed in a glass rack and immersed in a boiling (100° C.) water bath. After 24 hours (86,400 s), the test pieces were removed, blotted dry, weighed and then tested for flexural strength and modulus using the method of Example 5. The results are reported in Table IV wherein the unexposed (0 hr) values are provided for comparison.

COMPARATIVE EXPERIMENT E

A set of flexural test pieces (3) were prepared from a portion of the clear, unfilled casting of Comparative Experiment D. The test pieces were exposed to boiling water then tested using the method of Example 6. The exposure was simultaneous with that of Example 6. The results are reported in Table V.

TABLE IV

|  | Hours of Exposure to 100° C. Water | |
|---|---|---|
|  | 0 | 24 |
| Barcol Hardness | 46 | 33 |
| (% decrease) | — | (28.3) |
| Flexural strength, | | |
| psi | 17,353 | 13,623 |
| kPa | 120,000 | 93,900 |
| (% decrease) | — | (21.5) |
| Flexural Modulus, | | |
| psi | 573,000 | 516,000 |
| kPa | $3.95 \times 10^6$ | $3.56 \times 10^6$ |
| (% decrease) | — | (9.95) |

TABLE V

|  | Hours of Exposure to 100° C. Water | |
|---|---|---|
|  | 0 | 24 |
| Barcol Hardness | 38 | 24 |
| (% decrease) | — | (36.8) |
| Flexural strength, | | |
| psi | 19,734 | 10,759 |
| kPa | 136,000 | 74,200 |
| (% decrease) | — | (45.5) |
| Flexural Modulus, | | |
| psi | 420,000 | 397,000 |
| kPa | $2.90 \times 10^6$ | $2.74 \times 10^6$ |
| (% decrease) | — | (5.48) |

EXAMPLE 7

A. Preparation of Unsaturated Diimide

A solution of 1,2-diaminoethane (38.75 grams, 0.646 mole) and dimethylformamide (400 milliliters) was heated to 45° C. with stirring and maintained under a nitrogen atmosphere. Tetrahydrophthalic anhydride (196.30 grams, 1.29 moles) was added to the reactor over a 30 minute (1800 s) period after which time the reactor was heated to 90° C. and held for 30 minutes (1800 s). The reaction temperature was then increased to 130° C. and held for 30 minutes (1800 s) followed by decreasing the reaction temperature to 110° C. After 90 minutes (5400 s) at the 110° C. temperature, no further water was being recovered into the Dean Stark trap-cold water condenser assembly, hence the reactor was cooled to room temperature (26° C.). The reaction product was mixed with methanol (400 milliliters) and then chilled in an ice bath. The crystalline product was removed by filtration and washed with methanol. The white crystals were dried for 12 hours (43,200 s) at 100° C. until a constant product weight of 133.0 grams (63 percent yield) was recovered. Infra-red spectrophotometric analysis and nuclear magnetic spectroscopy confirmed the product structure for the diimide of tetrahydrophthalic anhydride.

B. Preparation of Imide Functional Polyphenol

Phenol (360.0 grams, 3.79 moles) and boron trifluoride etherate (2.0 grams) were heated to 120° C. with stirring and maintained under a nitrogen atmosphere. A portion of the diimide of tetrahydrophthalic anhydride (38.5 grams, 0.25 mole) was added to the reactor and the reaction temperature was increased to 160° C. and held for 8 hours (28,800 s). After this time, the excess phenol was vacuum distilled from the reactor. The product was placed in a 9 inch by 6 inch (228.6 mm × 152.4 mm) flat glass tray and dried under vacuum (50 millimeters Hg) for 18 hours (64,800 s) at 120° C. The polyphenol of the diimide of tetrahydrophthalic anhydride (75.3 grams, 99 percent yield) was recovered as a yellow colored, brittle transparent solid. Infra-red spectrophotometric analysis and nuclear magnetic resonance spectroscopy confirmed the product structure.

C. Preparation of Polycyanate of the Imide Functional Polyphenol

A portion of the diimide polyphenol (43.9 grams, 0.085 mole) was added to a reactor containing 170 milliliters of acetone and stirred under a nitrogen atmosphere. The diimide polyphenol-acetone solution was cooled to −5° C. then cyanogen bromide (18.91 grams, 0.1785 mole) was added to the reactor. The stirred solution was allowed to equilibrate at −5° C. then triethylamine (17.29 grams, 0.1708 mole) was added to the reactor over a 10 minute (600 s) period and so as to maintain the reaction temperature at −5° to 0° C. After completion of the triethylamine addition, the reaction temperature was maintained at −3° to 6° C. for an additional 20 minutes (1200 s), followed by addition of the reaction product to chilled water (2000 milliliters) with agitation. After 5 minutes (300 s) the water and product mixture was multiply extracted with methylene chloride. The combined methylene chloride extract was washed with 5 percent hydrochloric acid (300 milliliters), water (800 milliliters) and then dried over anhydrous magnesium sulfate. The dry methylene chloride extract was filtered and solvent removed by rotary evaporation under vacuum. The polycyanate of the polyphenol of the diimide of tetrahydrophthalic anhydride was recovered (37.91 grams) in 78.7 percent yield as a light orange colored, brittle transparent solid. Infra-red spectrophotometric analysis confirmed the product structure.

EXAMPLE 8

A pair of 12 inch × 12 inch (304.8 mm × 304.8 mm) woven fiberglass cloth pieces were equally impregnated with a solution prepared from 29.4 grams of the polycyanate of the imide functional polyphenol of Example 7-C, a polyepoxide (35.33 grams) chloroform (125 grams) and 0.215 grams of cobalt naphthenate (6.0 percent active). The polyepoxide had an epoxide equivalent weight (EEW) of 340.5 and was prepared by advancement reaction of bisphenol A diglycidyl ether (EEW=183) (0.40 mole, 146.4 grams) with bisphenol A (0.20 mole, 45.66 grams) and benzyltrimethylammonium chloride catalyst (60 percent aqueous) (0.19 gram) at 120° C. for 50 minutes (3000 s). A laminate was prepared using the method of Example 4 except that prepolymerization (B-staging) was performed for 30 minutes (1800 s) at 70° C., 15 min. (900 s) at 100° C., and ten minutes (600 s) at 150° C. The resulting laminate was rigid, light yellow-colored and transparent. Post-curing and mechanical property testing was completed using the method of Example 2. The results are reported in Table VI.

TABLE VI

| | Example 8 |
|---|---|
| Barcol Hardness | 65 |
| Flexural Strength, | |
| psi | 77.7 × 10³ |
| kPa | 536 × 10³ |
| Flexural Modulus, | |
| psi | 3.67 × 10⁶ |
| kPa | 25.3 × 10⁶ |

EXAMPLE 9

The diimide polyphenol of endomethylenetetrahydrophthalic anhydride and 1,2-diaminoethane (81.09 grams, 0.15 mole), epichlorohydrin (138.80 grams, 1.50 mole), isopropanol (35 percent by weight of epichlorohydrin used, 74.74 grams), and water (8 percent by weight of epichlorohydrin used, 12.07 grams) were added to a reactor and stirred under a nitrogen atmosphere at 70° C. until a solution was formed. The reactor was maintained at 70° C. and dropwise addition of a sodium hydroxide (21.60 grams, 0.54 mole) solution in water (86.40 grams) commenced and was completed over the next 45 minutes (2700 s). After 20 minutes (1200 s) of further reaction, a second solution of sodium hydroxide (9.60 grams, 0.24 mole) in water (38.40 grams) was added dropwise to the reactor over the next 20 minutes (1200 s). Twenty minutes (1200 s) later, the reactor was cooled to 50° C. then an initial water wash (600 grams) was added to the reactor. The reactor contents were transferred to a separatory funnel containing additional epichlorohydrin (200 grams). The water wash layer was separated and discarded while the organic layer was added back into the separatory funnel along with a second water wash (200 grams). The water wash layer was separated and discarded and the recovered organic layer was stripped of solvents by rotary evaporation at 100° C. for 60 minutes (3600 s) under vacuum. The epoxy resin was recovered (70.46 grams) as a transparent, light amber-colored, tacky solid at room temperature (25° C.). Infra-red spectrophotometric analysis confirmed the product structure and epoxide titration revealed 11.52 percent epoxide in the product.

EXAMPLE 10

Preparation of Imide Functional Polyphenol Using a 4 to 1 Mole Ratio of Phenol to Unsaturated Diimide Phenol (150.0 grams, 1.67 moles) and boron trifluoride etherate (3.0 grams) were heated to 120° C. with stirring and maintained under a nitrogen atmosphere. A portion of the diimide of endomethylenetetrahydrophthalic anhydride (147.0 grams, 0.412 moles) prepared using the method of Example 1-A was added to the reactor and the reaction temperature was increased to 160° C. and held for 480 minutes (28800 s). After this time, the excess phenol was vacuum distilled from the reactor (100° C. and 5 millimeter Hg). The product was then placed in a 9 inch by 6 inch (228.6 mm × 152.4 mm) flat glass tray and dried under vacuum (50 millimeters Hg) for 72 hours (259,200 s) at 100° C. During the vacuum drying, a small amount of unreacted diimide sublimed from the light yellow colored, brittle, transparent solid product. Nuclear magnetic resonance spectroscopy demonstrated incomplete conversion of the unsaturation of the unsaturated diimide starting reactant.

EXAMPLE 11

Portions (0.20 gram) of the imide functional polyphenols of Example 3-B and Example 10 were analyzed by size exclusion chromatography. A portion (0.20 gram) of the unsaturated diimide of Example 3-A was analyzed and used as a reference standard. The following results were obtained:

|  | Unsaturated Diimide (Area %) | Diimide Polyphenols (Area %) |
|---|---|---|
| Example 3-A (reference standard) | 100 | none |
| Example 3-B | none | 100 |
| Example 10 | 26.4 | 73.6[1] |

[1] Also includes diimide monophenols present

The diimide polyphenols from Example 3-B were further characterized by the size exclusion chromatographic analysis as containing 75.8 area percent of the diimide diphenols (Formula I where $n^1=0$) and 24.2 area percent of the diimide polyphenols (Formula I where $n^1=1$ to about 10). Minor amounts (less than 5 percent) of norbornyl unsaturation (attributed to compositions of the structure represented by Formula II) were detected by nuclear magnetic resonance spectroscopy in the diimide polyphenol product of Example 3-B.

EXAMPLE 12

A commercial grade of bisphenol A diglycidyl ether (219.60 grams, 0.60 mole) having an epoxide equivalent weight (EEW) of 183 was reacted with the diimide polyphenol (70.98 grams, 0.132 mole) of endomethylenetetrahydrophthalic anhydride and 1,2-diaminoethane to provide an advanced epoxy resin with imide functionality. The diimide polyphenol was prepared using the method of Example 3-A and 3-B. The diimide polyphenol, bisphenol A diglycidyl ether and 60 percent aqueous benzyltrimethylammonium chloride catalyst (0.29 gram) were added to a reactor and heated to 120° C. with stirring under a nitrogen atmosphere. After 60 minutes (3600 s) at the 120° C. reaction temperature, the reactor was cooled and the imide functional advanced epoxy resin was recovered as a transparent, light amber colored liquid. Epoxide titration revealed 15.13 percent epoxide in the resin. A portion of the epoxy resin (250.0 grams) was heated to 75° C. then methylene dianiline (43.54 grams) was added and thoroughly mixed in. The resulting solution was cured on a glass plate for 2 hours (7200 s) at 75° C. followed by post curing for 2 hours (7200 s) at 125° C., 2 hours (7200 s) at 175° C., then 2 hours (7200 s) at 200° C. Thermogravimetric analysis (TGA) of a 13.74 milligram portion of the cured product was performed. Weight loss was recorded as a function of temperature at a 10° C. per minute rate of increase in a stream of nitrogen flowing at 35 cubic centimeters per minute. The results are reported in Table VII.

TABLE VII

| Weight Loss (%) | | | | |
|---|---|---|---|---|
| 100° C. | 300° C. | 350° C. | 400° C. | 450° C. |
| 0.1 | 0.8 | 2.1 | 24.6 | 65.0 |

We claim:

1. A curable composition comprising
(A) any one or a combination of any two or more of the materials represented by the following formulas (I) and (II)

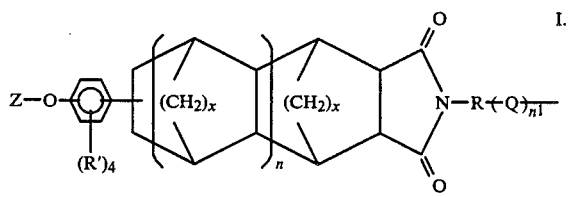

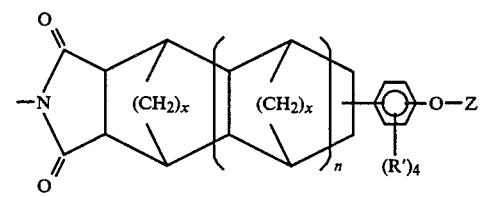

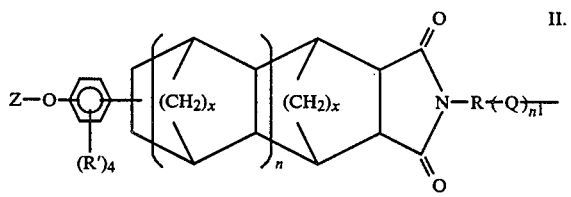

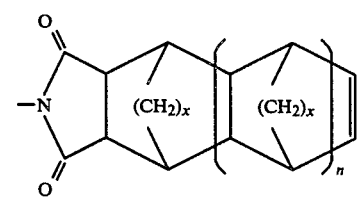

wherein each Q is independently

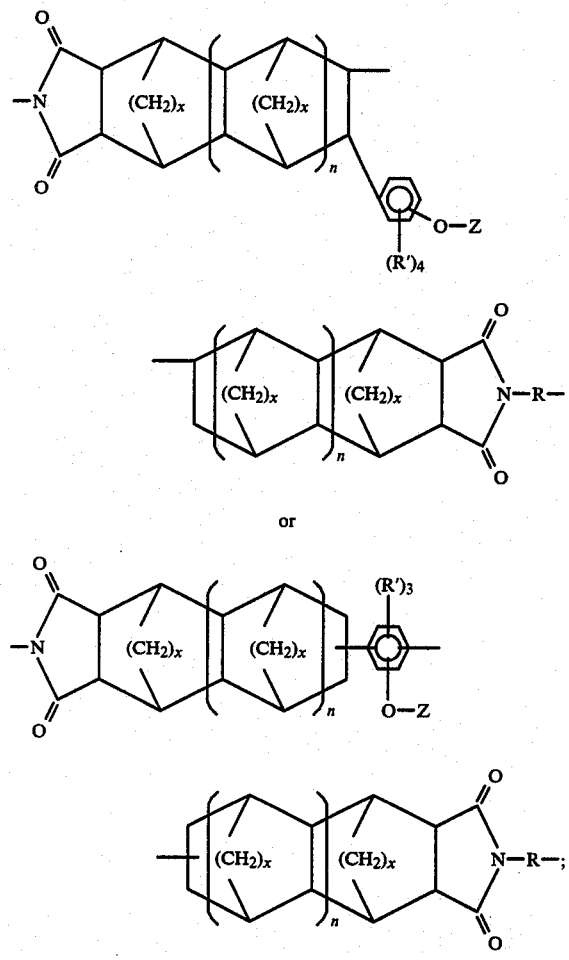

each R is independently a hydrocarbyl group having from 1 to about 10 carbon atoms, or a

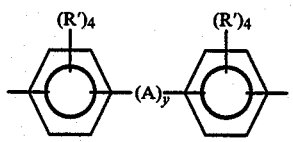

group; each A is independently a divalent hydrocarbyl group having from 1 to about 10, carbon atoms, $-S-$, $-S-S-$, $-O-$,

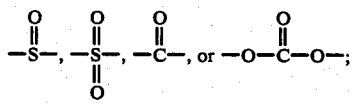

each R' is independently hydrogen, chlorine, bromine, a hydrocarbyl or hydrocarbyloxy group having from 1 to about 3 carbon atoms; each R'' is hydrogen or a hydrocarbyl group having from 1 to about 3 carbon atoms; Z is a group represented by the formula

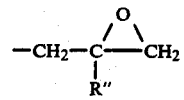

wherein R'' is hydrogen or a hydrocarbyl group having from 1 to about 4 carbon atoms; each x has a value of zero or 1; each y has a value of zero or 1; each n independently has an average value from zero to about 20, and $n^1$ has a value from zero to about 10;

(B) a curing quantity of at least one curing agent therefor.

2. A curable composition of claim 1 wherein component A comprises (1) from about 75 to about 100 percent by weight of a material represented by formula (I) wherein $n^1$ has a value of zero and (2) from about zero to about 25% by weight of any one or more of the materials represented by formulas (I) and (II) where $n^1$ has a value of from 1 to about 10.

3. A curable composition of claim 2 wherein each R is independently a hydrocarbyl group having from 2 to about 5 carbon atoms; each R' is hydrogen; each n independently has an average value from zero to about 8 and $n^1$ has a value from zero to about 2.

4. A curable composition of claim 3 wherein in component (A) each n has a value of zero.

5. A curable composition of claim 4 wherein in component (A) each x has a value of zero.

6. A curable composition of claim 4 wherein in component (A) each x has a value of one.

7. A curable composition of claim 3 wherein component (B) is bisphenol A, tetrabromobisphenol A or a mixture thereof.

8. A curable composition of claim 4 wherein component (B) is bisphenol A, tetrabromobisphenol A or a mixture thereof.

9. A curable composition of claim 5 wherein component (B) is bisphenol A, tetrabromobisphenol A or a mixture thereof.

10. A curable composition of claim 6 wherein component (B) is bisphenol A, tetrabromobisphenol A or a mixture thereof.

11. A product resulting from curing a composition of claims 1, 2, 3, 4, 5, 6, 7, 8 or 9.

12. A product of claim 11 which contains one or more reinforcing materials.

13. A product of claim 12 wherein said reinforcing material is glass, carbon, graphite or aramid.

* * * * *